(12) United States Patent  
Spearman

(10) Patent No.: US 8,702,658 B2
(45) Date of Patent: Apr. 22, 2014

(54) IV CATHETER INSERTION DEVICE AND METHOD

(76) Inventor: William L. Spearman, Beaufort, SC (US)

( * ) Notice: Subject to any disclaimer, the term of this patent is extended or adjusted under 35 U.S.C. 154(b) by 68 days.

(21) Appl. No.: 13/340,445

(22) Filed: Dec. 29, 2011

(65) Prior Publication Data

US 2013/0172820 A1    Jul. 4, 2013

(51) Int. Cl.
- *A61M 25/06* (2006.01)
- *A61M 5/31* (2006.01)
- *A61M 5/178* (2006.01)

(52) U.S. Cl.
CPC ... *A61M 25/0693* (2013.01); *A61M 2005/3112* (2013.01); *A61M 5/178* (2013.01)
USPC .................. 604/168.01; 604/165.01

(58) Field of Classification Search
CPC ............ A61M 5/178; A61M 25/0693; A61M 2005/3112
USPC ........................ 604/168.01, 165.01
See application file for complete search history.

(56) References Cited

U.S. PATENT DOCUMENTS

| | | | |
|---|---|---|---|
| 3,859,998 A | 1/1975 | Thomas et al. | |
| 4,003,403 A | 1/1977 | Nehring | |
| 4,193,399 A | 3/1980 | Robinson | |
| 4,200,096 A | 4/1980 | Charvin | |
| 4,269,186 A | 5/1981 | Loveless et al. | |
| 4,682,980 A | 7/1987 | Suzuki | |
| 4,765,588 A | 8/1988 | Atkinson | |
| 4,917,671 A | 4/1990 | Chang | |
| 4,935,010 A | 6/1990 | Cox et al. | |
| 5,032,116 A * | 7/1991 | Peterson et al. | 604/168.01 |
| 5,226,883 A | 7/1993 | Katsaros et al. | |
| 5,242,411 A | 9/1993 | Yamamoto et al. | |
| 5,290,246 A | 3/1994 | Yamamoto et al. | |
| 5,368,029 A | 11/1994 | Holcombe et al. | |
| 5,542,932 A | 8/1996 | Daugherty | |
| 5,575,777 A * | 11/1996 | Cover et al. | 604/198 |
| 5,730,123 A | 3/1998 | Lorenzen et al. | |
| 5,743,872 A * | 4/1998 | Kelly | 604/500 |
| 5,824,001 A * | 10/1998 | Erskine | 604/158 |
| 5,947,932 A | 9/1999 | Deseki et al. | |
| 6,156,010 A * | 12/2000 | Kuracina et al. | 604/168.01 |
| 7,736,342 B2 * | 6/2010 | Abriles et al. | 604/192 |
| 7,766,879 B2 * | 8/2010 | Tan et al. | 604/168.01 |
| 8,066,670 B2 | 11/2011 | Cluff et al. | |
| 8,070,725 B2 | 12/2011 | Christensen | |
| 2004/0181192 A1 | 9/2004 | Cuppy | |
| 2005/0043684 A1* | 2/2005 | Basta et al. | 604/164.13 |
| 2005/0273019 A1 | 12/2005 | Conway et al. | |
| 2007/0043334 A1 | 2/2007 | Guala | |
| 2007/0191777 A1 | 8/2007 | King | |
| 2007/0255221 A1* | 11/2007 | Nakajima | 604/168.01 |
| 2008/0215009 A1* | 9/2008 | Shaw et al. | 604/168.01 |

(Continued)

*Primary Examiner* — Laura Bouchelle
*Assistant Examiner* — Gerald Landry, II
(74) *Attorney, Agent, or Firm* — Kenneth A. Seaman

(57) ABSTRACT

An IV catheter insertion device includes a flash chamber into which blood (or other fluid) flows to confirm the proper placement of the catheter. Within the device is a movable member which is controlled from outside, as by a health care worker moving a plunger to move the movable member and expel blood from the flash chamber through the needle for testing or other analysis. The plunger may have a locking and unlocking mechanism to present the movement of the plunger from occurring when it is not desired.

30 Claims, 7 Drawing Sheets

(56) References Cited

U.S. PATENT DOCUMENTS

| | | |
|---|---|---|
| 2008/0255473 A1 | 10/2008 | Dalebout et al. |
| 2008/0287906 A1 | 11/2008 | Burkholz et al. |
| 2009/0099431 A1 | 4/2009 | Dalebout et al. |
| 2010/0262038 A1* | 10/2010 | Tan et al. .................. 600/576 |
| 2012/0016265 A1 | 1/2012 | Peterson et al. |
| 2012/0016307 A1 | 1/2012 | Burkholz et al. |
| 2012/0101440 A1* | 4/2012 | Kamen et al. ........... 604/164.08 |
| 2013/0184680 A1* | 7/2013 | Brewer et al. ............. 604/510 |

* cited by examiner

IV CATHETER INSERTION DEVICE AND METHOD

BACKGROUND OF THE INVENTION

A patient admitted to a hospital, an outpatient treatment center, or an outpatient surgery center will have an intravenous (IV) catheter inserted for easy access for fluids and drugs to be administered to the patient. The IV catheter is typically inserted using an IV insertion device, and some of these IV insertion devices have become known in the industry as JELCOs after the name of one company which brought these insertion devices to market. It is frequently necessary for a sample of the patient's blood to be obtained—e.g., for testing, blood typing or other analysis. For many of these blood tests, only a small sample of blood is required. After the IV catheter has been inserted, the healthcare worker may obtain this blood sample by various means. One method would be to have the patient endure another needle stick either by a needle and syringe to draw an aliquot of blood or by pricking the patient's finger with a lancet for a few drops of blood.

Some have proposed to use some of the blood that remains within the JELCO or IV catheter insertion device after the IV catheter has been inserted in a patient. Most IV catheter insertion devices include an integrated flash chamber. Red blood appears within the flash chamber of an IV catheter insertion device as the operator inserts the needle of the IV catheter insertion device into the vein to show that the IV catheter has entered a vein. The operator watches the flash chamber continuing to fill with blood as the operator advances the IV catheter into the vein, thereby ensuring the IV catheter remains properly positioned within the vein. Usually the proximal end of the flash chamber is blocked by a flash plug. The flash plug typically includes a filter material that allows air to vent from the flash chamber as the blood or fluid fills the chamber, but prevents the blood or fluid from passing from the flash chamber. IV catheter insertion devices of the prior art may have one of two different types of flash plugs. An IV catheter insertion device, such as described in U.S. Pat. No. 5,000,740, has a fixed or non-removable flash plug. Another type of prior art IV catheter insertion device is seen in U.S. Pat. No. 4,917,671 with a removable flash plug.

When an IV catheter has been placed within the vein, the remainder of the JELCO or IV catheter insertion device is removed from the patient. A small amount of the patient's blood remains within the flash chamber of the JELCO or IV catheter insertion device. By accessing the patient's blood from the flash chamber of the IV catheter insertion device, the operator may be able to avoid an additional needle stick to the patient. There are some known approaches to access blood in the flash chamber of an IV catheter insertion device. One such approach in IV catheter insertion devices with a non-removable flash plugs involves using an external probe, such as a pen or a golf tee, to push an internal flash plug within the flash chamber to expel blood from the flash chamber. The use of an external device such as a golf tee or pen is undesirable for several reasons. The external device must be stored some place that is easily accessible to the operator. The use of an external device is inefficient as the worker must look for or gather additional equipment when accessing the captured blood or fluid and replace the additional equipment for its next use. If the worker were to reuse any external probe or device (including a pen or a golf tee), cross-contamination may occur from one flash chamber to another, putting other patients and the healthcare worker at risk.

In IV catheter insertion devices that have removable flash plugs, another prior art approach to access the blood in a flash chamber requires the healthcare worker to remove the flash plug, thereby opening the flash chamber to access the blood within the flash chamber for testing. This action may unnecessarily expose the healthcare worker to hazardous material (such as blood or other bodily fluid) that may spill from the flash chamber.

While various prior art methods may allow the healthcare worker to access the blood or fluid within the flash chamber of an IV catheter insertion device (or JELCO), these methods present inefficient and undesirable aspects and limitations to the health care worker.

The present invention addresses some of these undesirable limitations and aspects to provide an improved device and method for accessing blood from an IV catheter insertion device without the use of undesirable additional hardware and without unnecessary risks. This new method and device will thereby increase the efficiency of the healthcare worker and reduce the hazardous exposure of bodily fluids to the workers and patients.

SUMMARY OF THE INVENTION

The present invention provides a system and method for providing a self-contained system for removing blood (or other fluid) from an IV catheter insertion device (or JELCO) in a controlled manner upon demand and with greater ease and less risk to the worker.

The present invention has the advantage of reducing the number of needle sticks to a patient by using blood or bodily fluid that has been collected within the IV catheter insertion device when the IV catheter is placed. That is, the fluid sample used for testing is a by-product of the use of the IV catheter insertion device.

Applicant teaches in this patent application that blood collected within the flash chamber of an intravenous catheter insertion device can be accessed with an integral structure safely and efficiently. The blood or fluid thus collected can be used for analysis or testing without requiring the healthcare worker to inflict additional needle sticks to a patient.

It is desirable that an IV catheter insertion device (or JELCO) be simple to make and maintain in a sterile condition. It is also desirable that the device be self-contained and not require additional tools, e.g., an external device like a golf tee in order to access the blood contained in the flash chamber.

It is also desirable that the operator be able to access the blood or fluid within the IV catheter insertion device without having to open the flash chamber, thereby reducing the chance for exposure of hazardous material to the worker and patient.

The present invention overcomes the disadvantages and limitations of the prior art systems while providing a simple, yet effective, way of accessing the blood contained in the flash chamber of an IV catheter insertion device for testing and analysis.

Other objects and advantages of the present invention will be apparent to those of ordinary skill in the art in view of the following detailed description of the preferred embodiment taken in conjunction with the accompanying drawings.

BRIEF DESCRIPTION OF THE DRAWINGS

FIG. 1b is a cross sectional view of the IV catheter insertion device of FIG. 1a;

DETAILED DESCRIPTION OF THE PREFERRED EMBODIMENT

The following illustrates the use of the preferred embodiment of this new method and device.

Figure 1A:
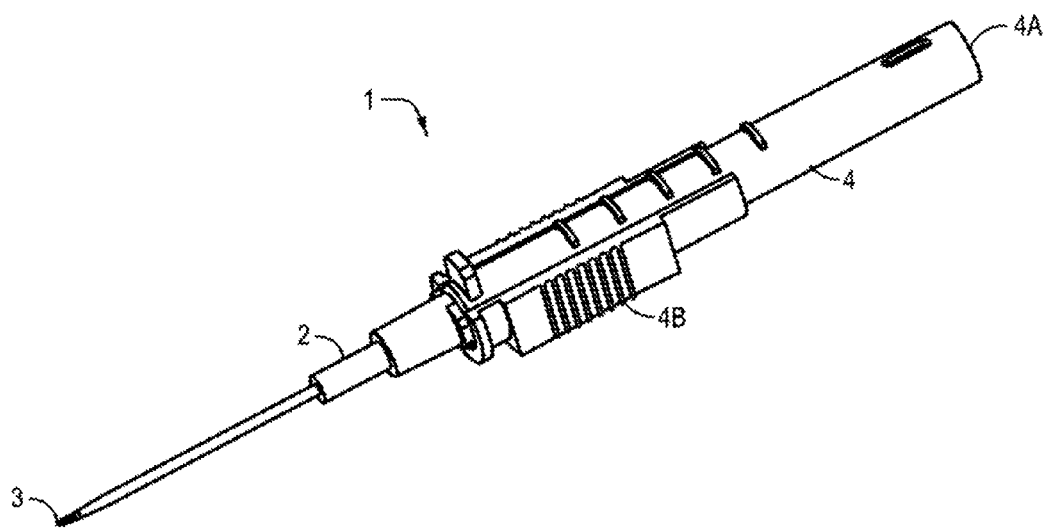
FIG. 1a is a perspective view of one type of prior art IV catheter insertion device (a JELCO)

FIG. 1a illustrated one example of a prior art IV catheter insertion device (which medical personnel sometimes referred to as a "JELCO") 1. The IV catheter insertion device 1, shown enlarged and in perspective in this view, includes an IV catheter 2, a distal end 3 and a barrel 4 at a proximal end 4a. This FIG. 1a illustrates one example of an IV catheter insertion device 1 having a non-removable flash plug at the proximal end of a flash chamber (not shown in this view), the construction and operation of an example of which system is more fully described in detail in U.S. Pat. No. 5,000,740, the specification and drawings of which are specifically incorporated herein by reference.

Figure 1B:
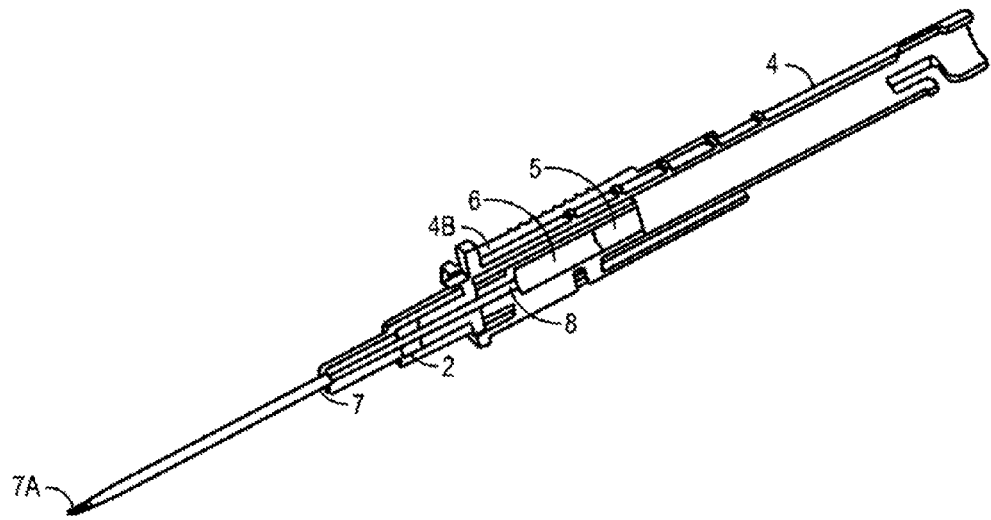

FIG. 1b depicts more detail for the IV catheter insertion device 1 of one prior art JELCO which forms one environment for the present invention. This FIG. 1b shows a cut-away view of the IV catheter insertion device 1 shown in FIG. 1a and includes the barrel 4, a flash plug 5, a flash chamber 6, and a needle 7 with a distal tip 7a and a proximate end 8 which communicates with the flash chamber 6. The barrel 4 of the IV catheter insertion device 1 and the flash chamber 6 are both formed from a transparent material, such as a plastic, so that one can clearly see through the barrel 4 into the flash chamber 6, so that when blood enters into the flash chamber 6, the red color of the blood is clearly visible outside the IV catheter insertion device 1. The needle 7 includes an internal aperture extending from its distal tip 7a to its proximate end 8 adjacent the flash chamber 6, so that when distal tip 7a of the needle 7 is properly inserted within a patient's vein (not shown), blood from the vein can enter the flash chamber 6 (and be visible to an observer looking from outside the IV catheter insertion device 1).

Figure 2:
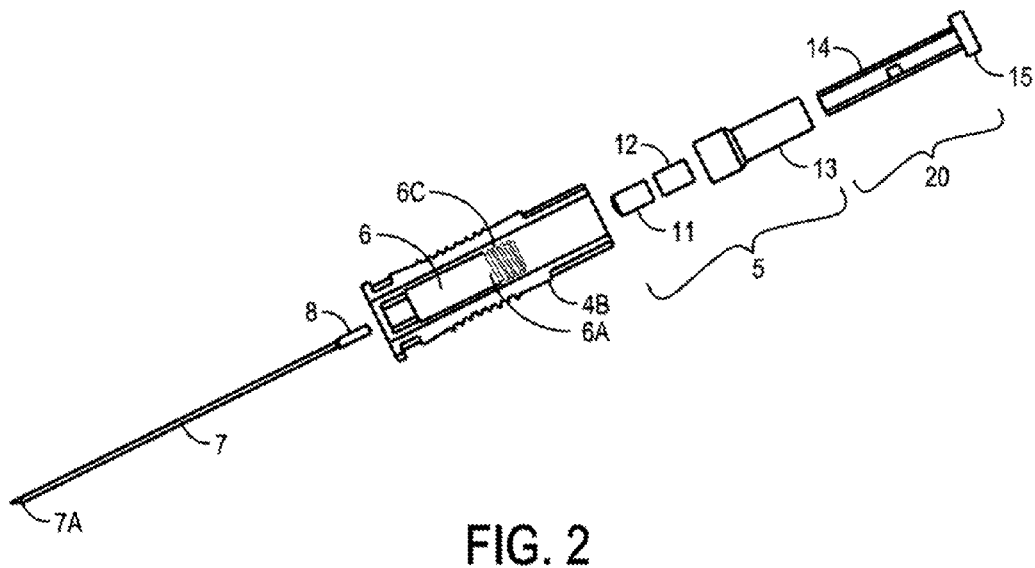
FIG. 2 is an exploded view of portions of the IV catheter insertion device of FIGS. 1a and 1b, modified to include one form of the present invention.

FIG. 2 is an exploded view of selected components of the IV catheter insertion device 1 of the present invention (but not all of the components). The needle 7 includes its distal tip or end 7a and a proximate end 8 which is secured within the flash chamber 6 of the IV catheter insertion device 1. The flash chamber 6 is contained within the barrel handle 4b and is shown with screw threads 6c at the proximate end 6a of the flash chamber 6. The flash plug 5 comprises a flash plug filter 11, a rubberized seal 12 and a cap 13. The cap 13 includes internal threads (not shown) which couple with the screw threads 6c on the flash chamber 6 when the device 1 is fully assembled and ready for use. The proximate end 8 of the needle is secured within the flash chamber 6 and sealed so that the blood flows from the distal end 7a of the needle 7 to the flash chamber 6 where it is secured. A plunger 20 is formed by a shaft 14 and a handle 15 and is mounted through a central aperture in the cap 13. This plunger 20, through its shaft 14 and handle 15, can be moved by a user through apertures extending through the cap 13 and the rubberized seal 12 to press against the flash plug filter 11 and move the flash plug filter 11 away from the operator within the flash chamber 6 to expel blood, as desired, from the distal end 7a of the needle 7.

Figure 3:
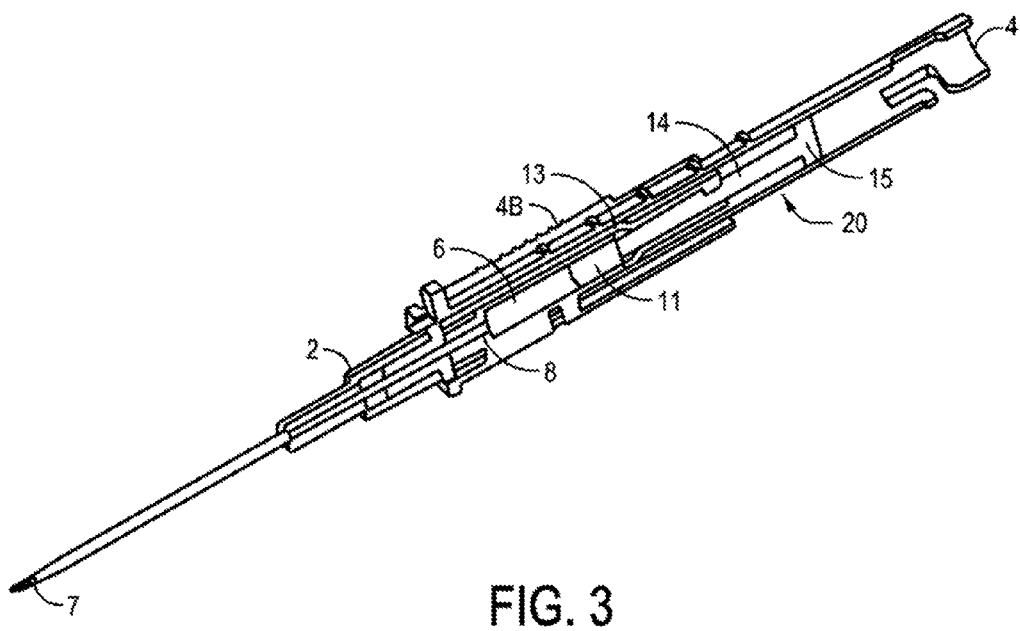
FIG. 3 is a cross sectional view of the IV catheter insertion device of FIGS. 1a, 1b and 2, showing one form of the present invention.

In one preferred embodiment as seen in FIG. 3, the plunger 20 including the shaft 14 and the handle 15 extend through the cap 13 which can be seen coupled to the proximal portion of the flash chamber 6. The healthcare worker, or operator, uses the IV catheter insertion device 1 to insert an IV catheter in the usual manner. As the operator inserts the needle tip 7a into the vein, the flash chamber 6 fills with blood. In this embodiment, as the operator advances the IV catheter, the barrel 4 (which serves as a needle guard) advances distally over the distal tip 7a of the needle 7. As the barrel or needle guard 4 advances distally over the needle 7, the shaft 14 and handle 15 of the invention becomes exposed for the operator. With the IV catheter insertion device 1 in this locked position, the operator can position the distal tip 7a of the needle 7 over a testing strip or blood receiving cassette. The operator then grasps the handle 15 and rotates the shaft 14 and handle 15 enough to disengage the shaft 14 from its locked position. Using the handle 15, the operator advances the shaft 14 and plunger 20 from the proximal position in the flash chamber 6 to the distal position of the flash chamber 6. The action of moving the shaft 14 and plunger 20 from its retracted position to its forward position will force the blood or fluid within the flash chamber 6 back through the needle 7 and to exit at the distal tip 7a of the needle 7. As the blood or fluid is expressed from the needle tip 7a, the operator can direct this blood or fluid onto a testing strip or other blood receiving container such as a cassette or cartridge. The entire IV catheter insertion device 1 (other than the IV catheter 2, which remains within the vein of the patient) can then be disposed of properly into a hazardous waste container.

Figure 4:
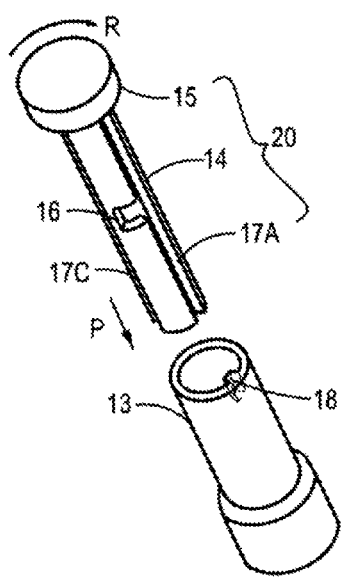
FIG. 4 is a perspective, exploded view of portions (one example of a plunger and cap assembly) of the invention, prior to assembly of them into the IV catheter insertion device.

FIG. 4 shows detail of the plunger 20 including the shaft 14 and the handle 15 as used in the environment of FIGS. 1a-3 as described above. The shaft 14 includes a plurality of grooves extending along the length of the shaft 14, two of which are shown in this FIG. 4 as reference numerals 17a and 17c. A notch 16 cooperates with one groove 17a to form a locking mechanism in cooperation with a projection 18 in the cap 13. The plunger 20 is initially locked with the projection 18 fitting within the notch 16, then the operator rotates the handle 15 of the plunger 20 in the direction of the arrow R to release the locking mechanism and allow the plunger 20 including shaft 14 and handle 15 to move in the direction of arrow P along the length of the shaft by allowing the projection 18 to move along the groove 17a.

Figure 5:
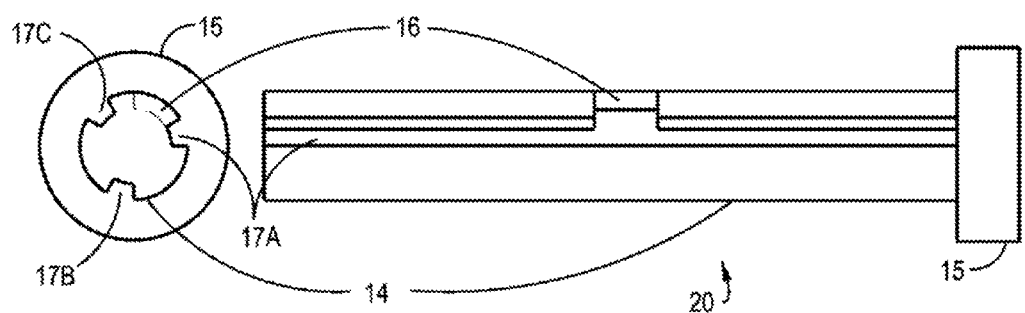
FIG. 5 shows side and bottom views of the plunger of FIG. 4.

FIG. 5 illustrates the elements of FIG. 4 in a bottom view and a side view to better understand the present invention. As shown here, the plunger 20 includes an enlarged handle 15 which is generally round and fits within the barrel 4 of the IV catheter insertion device 1. The shaft 14 is also generally cylindrical and of a smaller diameter to fit within an aperture through the cap 13 which fits within the barrel 4 of the device 1. Grooves 17a, 17b, 17c are shown disposed around the periphery of the shaft 14. The notch 16 is adjacent to and cooperating with one groove 17a to provide a locking (and releasing) mechanism for the plunger 20 along the length of the shaft 14.

Figure 6:
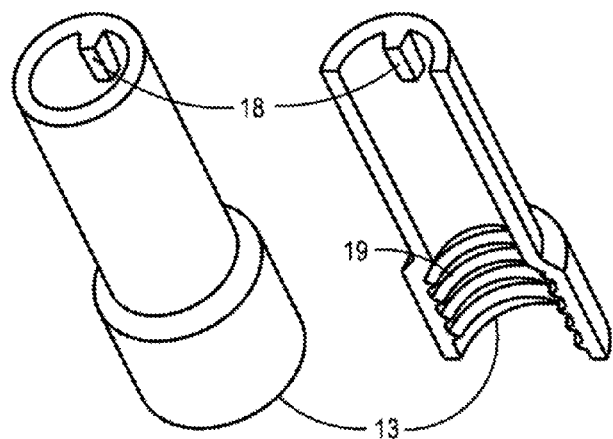
FIG. 6 is a perspective and cutaway view of the cap shown in FIG. 4.

FIG. 6 are a perspective view and a cut-away view which illustrate detail of the cap 13 and its projection 18 which cooperates with the notch 16 to provide locking and unlocking the shaft 14 of the plunger 20 and, when unlocked, allows the shaft 14 of the plunger 20 and the flash plug 11 to move forward within the flash chamber 6. The cap 13 includes internal screw threads 19 which mate with the screw threads 6c of the flash chamber 6 when the device is assembled.

Figure 7:
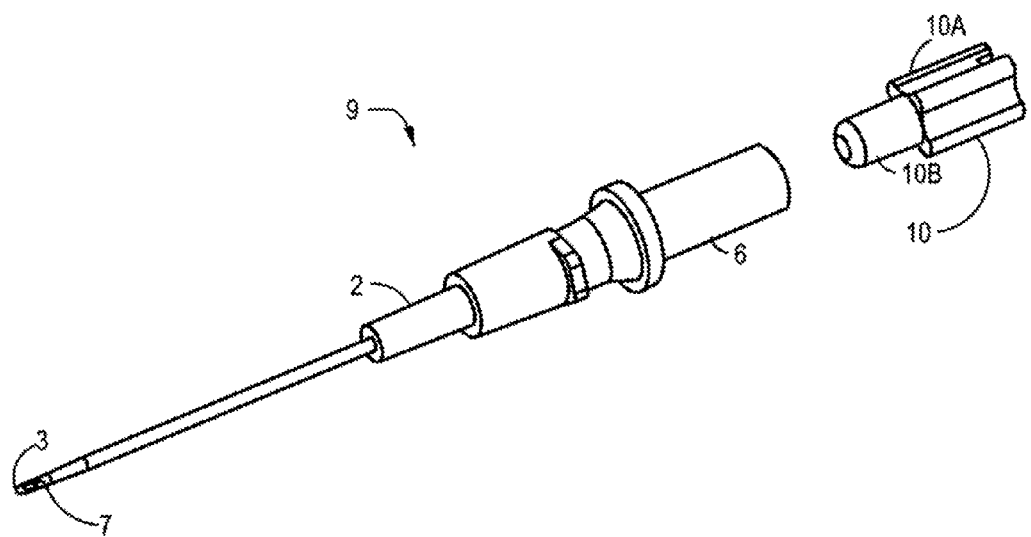
FIG. 7 is a perspective, exploded view of an alternate type of prior art IV catheter insertion device having a removable flash plug.

In another embodiment, the present invention can be used in conjunction with an alternate IV catheter insertion device 9 which includes a removable flash plug 10 as is illustrated in FIG. 7. FIG. 7 shows some of the components in a prior art IV catheter insertion device 9 of the type described in connection with U.S. Pat. No. 4,917,671, a patent whose drawings and specification are incorporated herein by reference. The IV catheter insertion device shown in this FIG. 7 includes the IV catheter 2, the needle 7 extending from the distal needle tip 7a at its distal end 3 to its flash chamber 6 with a removable flash plug 10. The removable flash plug 10 has a handle 10a and a leur tip 10b which connects within the flash chamber 6. The present invention involves substitution/modification of a modified plunger assembly 20a including a handle 15a and a removable flash plug for the flash plug 10 shown in this FIG. 7 as will be described in connection with later illustrations, particularly FIGS. 8-10. This substitution can occur, as desired, either during the initial manufacture and assembly of the IV catheter insertion device 9 or at the point of use e.g., bedside, using sterile techniques, preferably immediately prior to the operator inserting the IV catheter into the patient.

Figure 8:
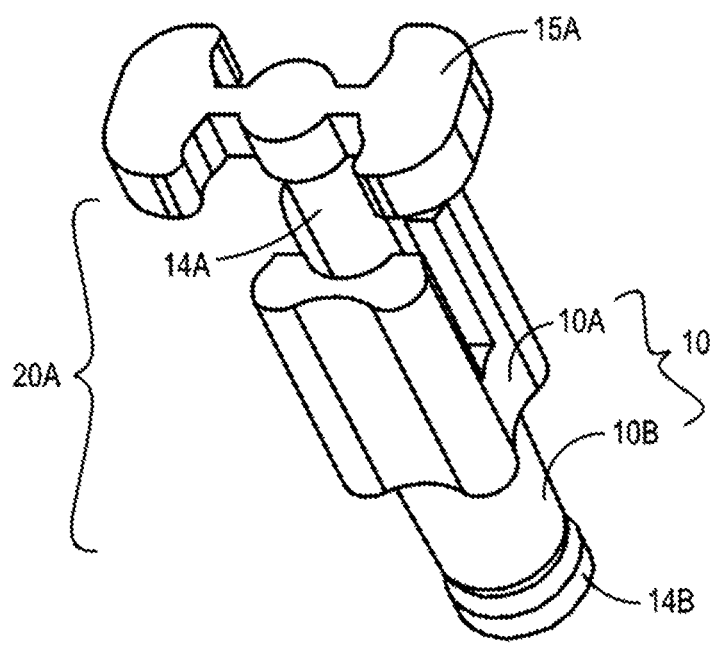
FIG. 8 is a perspective view of an assembly of the removable flash plug of FIG. 7, augmented with a plunger of the present invention in its primary position.

FIG. 8 shows the handle 15a and the shaft 14a of the modified plunger assembly 20a in their initial position extending through the removable flash plug 10 with its handle 10a and its leur tip 10b. A shaft end piece 14b is mounted on the other side of the leur tip 10b from the handle 15a.

Figure 9:
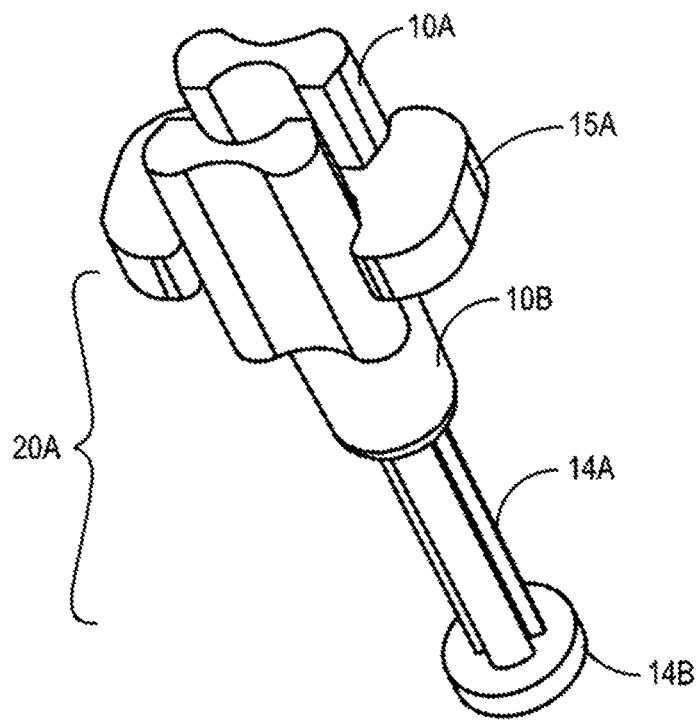
FIG. 9 is a perspective view of the removable flash plug and plunger of FIG. 8 with the plunger extended to its secondary position.

FIG. 9 shows the relative positions of the handle 15a, shaft 14a, the shaft end piece 14b, and the flash plug 10 when the plunger 20a has been extended (when it has been moved to expel blood from the flash chamber 6, not shown in this view). A significant portion of the shaft 14a extends below the leur tip 10b. The shaft end piece 14b consists of filter material to allow air to vent and prevents fluid from escaping.

Figure 10:
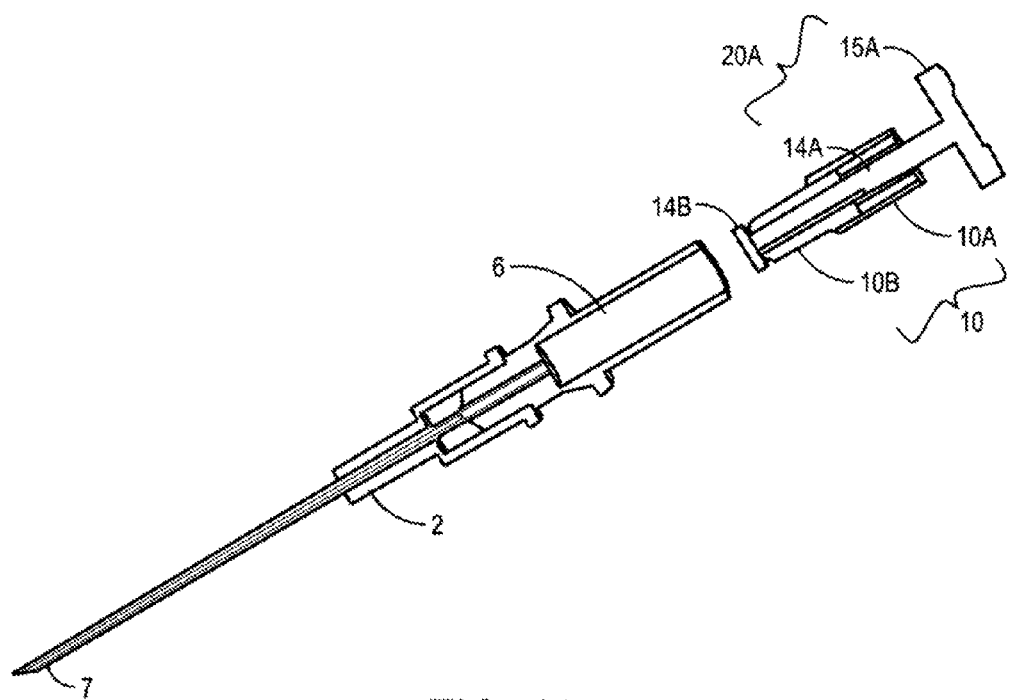
FIG. 10 is a perspective view of the removable flash plug and plunger of FIG. 9 being inserted into the alternate type of IV catheter insertion device shown in FIG. 7.

FIG. 10 shows the components of the IV insertion device 9 of the present invention in an exploded view. As shown here, the IV insertion device 9 includes a needle 7, an IV catheter 2, a flash chamber 6 and the plunger assembly 20a of FIGS. 8-9 with the handle 15a and the shaft 14a.

Figure 11:
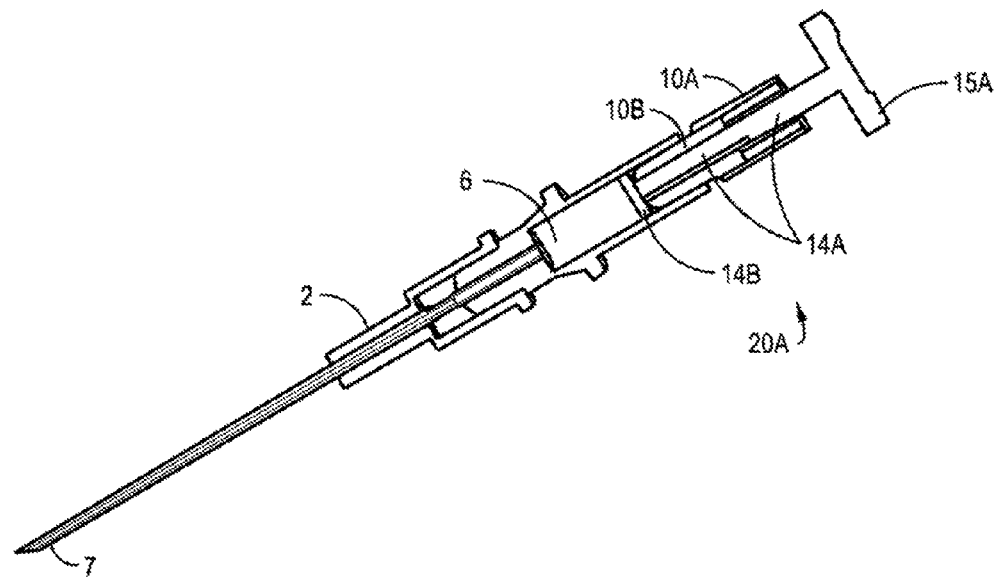
FIG. 11 is a view of the components of FIG. 10 assembled together.
Figure 12:
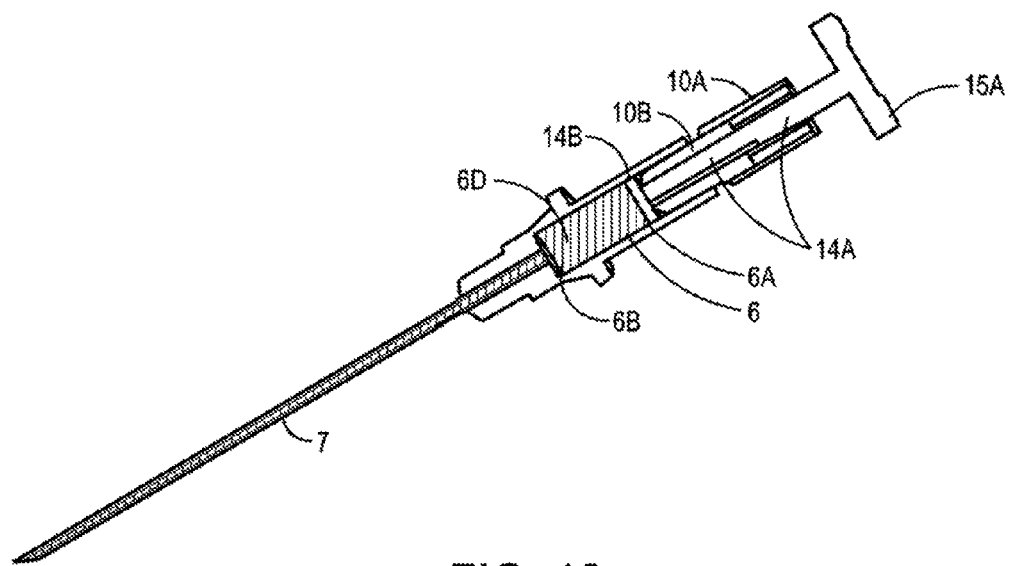
FIG. 12 is a view of the IV catheter insertion device after insertion of the IV catheter has been inserted and the remainder of the device removed.
Figure 13:
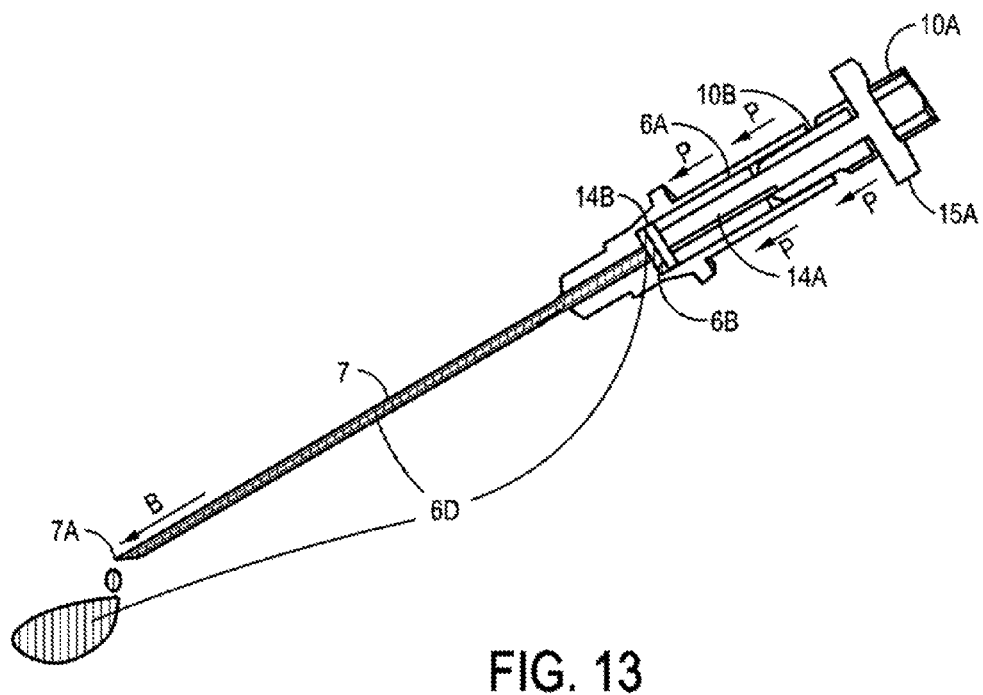
FIG. 13 is a view of the IV catheter insertion device of FIG. 12 with the plunger moved forward to expel blood (or other fluid) from the flash chamber of the insertion device.

FIGS. 11-13 show the IV catheter insertion device 9 as discussed in connection with FIGS. 7-10 wherein FIG. 11 shows the device prior to insertion of the IV catheter into a patient, FIG. 12 shows the device 9 after the IV catheter has been inserted into a patient and blood appears within the flash chamber 6 and the IV catheter 2 removed, and then FIG. 13 shows the device of FIG. 12 with the handle 15a moved forward in the direction of arrow P to expel blood from the flash chamber 6 to the distal end 7a of the needle 7 as indicated by the arrow B. Initially in FIG. 11 the plunger 20a including the handle 15a and the shaft 14a are at a rear or withdrawn position and preferably locked against accidental movement of the plunger 20a. After the IV is inserted into the patient, the IV catheter 2 is detached from the remainder of the IV insertion device 9 and the flash chamber 6 has become filled with blood 6d and the flash plug 14b is at the rear or proximate end of the flash chamber 6. The handle 15a and shaft 14a may be unlocked by rotating them to release them from the locking mechanism and moved forward or distally from the original position to a position as shown in FIG. 13. As the shaft 14a and handle 15a are moved forward, the shaft end (filter) 14b is also moved forward and urges the blood from the flash chamber 6 distally through the needle 7 out its distal tip 7a, where drops of blood 6d are shown.

An example of this embodiment can be seen in FIGS. 8-10. These figures illustrate from proximal to distal, a shaft handle 15a, a shaft 14a, a handle 10a with a luer-tip connector 10b through which the shaft 14a passes. The shaft 14a and handle 15a form a plunger 20a cooperating with the with filter material 14b to vent air as blood enters the flash chamber but prevents blood or fluid from escaping through the flash plug 10. The plunger may or may not have a rubberized seal to seal the plunger within the walls of the flash chamber 6. In this embodiment, the standard flash plug 10 has been removed and replaced by the assembly of the present invention 20a including the handle 10a with the plunger having its handle 15a and shaft 14a which has been inserted into and secured within the flash chamber 6 using the luer connector 10b. The operator is then ready to insert the IV catheter 2. The operator will insert the IV catheter 2 in the usual manner. After the IV catheter 2 has been inserted and secured, the operator removes the remainder of the IV insertion device 9. The operator then moves the deployed IV catheter insertion device 9 with blood or fluid within the flash chamber 6 to a position over a testing strip or cassette. The operator will grasp the handle 15a and rotate the handle 15a and the shaft 14a enough to unlock the locking mechanism. The operator will then push the handle 15a to move the shaft 14a and filter 14b at the distal end of the shaft 14a within the flash chamber 6 from the proximal position 6a within the flash chamber 6 (FIG. 12) to the distal position 6b within the flash chamber 6 (FIG. 13). The movement of the shaft 14a and filter 14b in the direction of arrows P from the position of FIG. 12 to the position of FIG. 13 will force the blood or fluid through the needle 7 in the direction of the arrow B toward the distal end 7a of the needle 7. As the blood or fluid (represented by drops of blood 6d) is expressed from the distal tip 7a of the needle 7, the operator can direct this blood or fluid 6d onto a testing strip or cassette (not shown). The operator can then dispose of the entire IV insertion device 9 (with the IV catheter 2 removed and remaining installed within the patient) into a hazardous materials container. Because the invention has replaced the removable flash plug 10 prior to insertion of the IV catheter 2, the operator can access the blood or fluid 6d within the flash chamber 6 without opening the flash chamber 6 or removing the flash plug 10, thereby reducing the possibility of exposure of hazardous material to the operator or patient.

Of course, many modifications to the best mode described above may be effected without departing from the spirit of my invention. Further, some of the features disclosed may be useful without the corresponding use of other features. For example, the use of an internal plunger within a rigid chamber could be replaced with a flexible flash chamber with an external, but integral, compression device for squeezing the flash chamber to expel blood out of the flash chamber. Further, the specific construction of the plunger and its coupling to the flash plug could be changed to advantage in some alternate embodiments of the present invention, and any locking and unlocking of the plunger is optional, as is any system for limiting the advance of the plunger. Further, if desired, the plunger could be provided with a system which limits the speed at which the plunger moves forward to provide a controlled method for expelling blood or other fluid from the flash chamber, even to the extent of limiting the blood removal to a drop at a time. The materials of the IV catheter insertion device including the barrel and the flash chamber are typically made from a transparent plastic material for easy of manufacture and durability as well as easy visual inspection of the flash chamber, but other materials, including glass, could be used for the barrel and the flash chamber, and need not be wholly transparent (a window or a translucent system might be used to advantage, if desired). Many other modifications could be used to advantage in some cases involving the present invention. Additionally, a different access point to the blood in the flash chamber could be used, if desired, in some instances. For example, an aperture with a cover in the wall of the flash chamber and/or the barrel of the insertion device might be opened to access the blood contained in the flash chamber and allow for an operator to expel blood on demand using a plunger or other pressure-applying force to remove blood through the aperture and cover, a system which avoids exposing the sharp needle of the catheter insertion device. Additionally, the insertion device has been described in connection with a catheter insertion device which accesses blood from a vein, but the present invention would also be applicable to a device which accesses other body fluids, such as spinal fluid, pleural fluid, ascites, other body fluids, or even some body tissues. Accordingly, the foregoing description of the preferred embodiment should be considered as merely illustrative of the principles of the present invention and not in limitation thereof. The scope of the present invention is to be determined solely by the claims which follow.

Having thus described the invention, what is claimed is:

1. A catheter insertion device comprising a housing carrying a needle, a flash chamber connected to the needle with a flash plug filter, the flash chamber providing a visual indicator of fluid when the needle of the catheter has been inserted into a fluid supply, and further including a movable member mounted to the housing and coupled to the flash chamber, said movable member moving from a first position to a second position within the flash chamber to expel fluid for testing from the flash chamber, said movable member being moved after fluid is within the flash chamber to expel fluid.

2. A catheter insertion device of the type described in claim 1 wherein the flash chamber includes a vent in front of or behind the movable member, the vent allowing the movable member to move to expel the fluid without creating a vacuum.

3. A catheter insertion device of the type described in claim 1 wherein the flash chamber includes a vent in front of or behind the movable member, the vent allowing air to escape the flash chamber as the chamber fills with blood or fluid while blocking the blood or fluid from escaping the chamber.

4. A catheter insertion device of the type described in claim 1 wherein the movable member is located toward the proximal portion of the flash chamber and is moved distally toward the needle to force fluid from the chamber.

5. A catheter insertion device of the type described in claim 1 wherein a lever coupled to the movable member extends through the housing and movement of the lever causes movement of the movable member to expel fluid from the flash chamber.

6. A catheter insertion device of the type described in claim 1 wherein the movable member is coupled to the flash chamber thereby not requiring the operator to open the flash chamber to access the blood or fluid within the flash chamber.

7. A catheter insertion device of the type described in claim 1 and further including a locking/unlocking mechanism to selectively restrict movement of the movable member from the first position.

8. A catheter insertion device of the type described in claim 7 where the locking mechanism includes a notch on the movable member and a projection associated with the housing, with the projection on the movable member fits within the notch in one position, but the movable member may be moved to release the projection from the latch to allow the movable member to become unlocked.

9. A catheter insertion device of the type described in claim 8 wherein the movable member has a rotary motion to release the projection from the notch to allow the movable member to become unlocked.

10. A catheter insertion device of the type described in claim 1 wherein the movable member includes a handle and a shaft, with the shaft coupling to a flash plug to move the flash plug within the flash chamber to expel fluid from the flash chamber through the needle.

11. A catheter insertion device of the type described in claim 10 wherein the movable member includes structure which restricts its movement and a release mechanism to allow the movable member to move.

12. A catheter insertion device of the type described in claim 11 wherein the housing has a cylindrical shape and the movable member includes a handle which is mounted for rotational movement with respect to an axis of the housing and for translation along the axis of the housing, with the rotational movement about the axis allowing for the release of the structure which restricts its movement and allows for translation along the axis of the housing when it is released.

13. A catheter insertion device of the type described in claim 1 wherein the flash chamber includes a flash plug which is not removable and the movable member moves the flash plug within the flash chamber to expel blood from the flash chamber.

14. A catheter insertion device of the type described in claim 1 wherein the flash chamber includes a flash plug which is removable and the movable member fits through the flash plug to move the flash plug within the flash chamber from a first position to a second position, where the movement to the second position serves to expel fluid from the flash chamber.

15. A method of using a catheter insertion device including a needle and a flash chamber connected to the needle to provide a show of blood within the flash chamber as an indication that the intravenous catheter has been inserted within a vein, the flash chamber having a flash plug with a filter, the improvement comprising the steps of:
    securing a moveable member to the catheter insertion device and adjacent the flash chamber behind the show of blood and the flash plug;
    moving the movable member forward toward the needle to urge the blood out of the flash chamber to controllably release blood from the flash chamber through the needle; and
    testing the blood.

16. A method of using a catheter insertion device including the steps of claim 15 and further including the step of unlocking the movable member.

17. A method of using a catheter insertion device including the steps of claim 16 wherein the step of unlocking the movable member includes the step of rotating the movable member.

18. A method of using a catheter insertion device including the steps of claim 17 wherein the step of rotating the movable member includes the step of positioning a fixed projection on one of the housing and the movable member within a slot to allow the movable member to translate along the axis of the housing.

19. A method of using a catheter insertion device to provide a sample of fluid from a patient, the catheter insertion device having a housing with a needle, a flash chamber coupled to the needle to receive fluid during the insertion of the catheter and a flash plug to allow gas to escape from the flash chamber while retaining the fluid within the flash chamber, the steps of the method comprising:
   integrating a movable member within the housing and positioning the movable member adjacent to the flash chamber and cooperating with the flash plug; and
   after the catheter has been inserted in the patient and the flash chamber contains fluid from the patient, moving the movable member and flash plug to expel fluid from the flash chamber through the needle.

20. A method of using a catheter insertion device including the steps of claim 19 and further including the step of providing the movable member with a locking mechanism to restrict its motion while locked and an unlocking mechanism to allow the movable member to move within the housing.

21. A method of using a catheter insertion device including the steps of claim 20 wherein the method includes the step of unlocking the movable member by rotating the member within the housing to release it from its locking mechanism.

22. A catheter insertion device comprising a housing carrying a needle, a flash chamber connected to the needle, the flash chamber providing a visual indication of fluid when the needle of the catheter has been inserted into a fluid supply, and further including a movable member mounted to the housing and coupled to the flash chamber, said movable member moving from a first position to a second position within the flash chamber to expel fluid from the flash chamber, said movable member being moved after fluid is within the flash chamber to expel fluid, further including a lever coupled to the movable member extending through the housing and movement of the lever causes movement of the movable member causes movement of the movable member to expel fluid from the flash chamber.

23. A catheter insertion device of the type described in claim 22 wherein the flash chamber includes a vent in front of or behind the movable member, the vent allowing the movable member to move to expel the fluid without creating a vacuum.

24. A catheter insertion device of the type described in claim 22 wherein the movable member includes a handle and a shaft and the movable member with the shaft coupling to a flash plug to move the flash plug within the flash chamber to expel fluid from the flash chamber, said movable member including structure which restricts its movement and a release mechanism to allow the movable member to move, wherein the housing has a cylindrical shape and the movable member includes a handle for rotational movement with respect to an axis of the housing and for translation along the axis of the housing, with the rotational movement along the axis allowing for the release of the structure which restricts its movement and allows for translation along the axis of the housing when it is released.

25. A catheter insertion device of the type described in claim 22 wherein the flash chamber includes a flash plug which is not removable and the movable member moves the flash plug within the flash chamber to expel blood from the flash chamber.

26. A method of using a catheter insertion device including a needle and a flash chamber connected to the needle to provide a show of blood within the flash chamber as an indication that the intravenous catheter has been inserted within a vein, the flash chamber having a flash plug and flash plug filter, the improvement comprising the steps of:
   securing a movable member to the catheter insertion device and adjacent the flash chamber, flash plug and flash plug filter, behind the show of blood;
   unlocking the movable member; and
   moving the movable member forward toward the needle to urge the blood out of the flash chamber to controllably release blood from the flash chamber through the needle.

27. A method of using a catheter insertion device including the steps of claim 26 wherein the step of unlocking the movable member includes the step of rotating the movable member.

28. A method of using a catheter insertion device including the steps of claim 27 wherein the step of rotating the movable member includes the step of positioning a fixed projection on one of the housing and the movable member within a slot to allow the movable member to translate along the axis of the housing.

29. A method of using a catheter insertion device to provide a sample of fluid from a patient, the catheter insertion device having a housing with a needle to receive fluid during insertion of the catheter and a flash plug to allow gas to escape from the flash chamber while retaining the fluid within the flash chamber, the steps of the method comprising:
   integrating a movable member within the housing and positioning the movable member adjacent to the flash chamber and cooperating with the flash plug;
   providing the movable member with a locking mechanism to allow the movable member to move within the housing; and
   after the catheter has been inserted in the patient and the flash chamber contains fluid from the patient, moving the movable member an the flash plug to expel fluid from the flash chamber through the needle.

30. A method of using a catheter insertion device including the steps of claim 29 wherein the method includes the step of unlocking the movable member by rotating the member within the housing to release it from its locking mechanism.

\* \* \* \* \*